(12) United States Patent
Gustafson

(10) Patent No.: US 9,171,130 B2
(45) Date of Patent: Oct. 27, 2015

(54) MULTIPLE MODALITY MAMMOGRAPHY IMAGE GALLERY AND CLIPPING SYSTEM

(75) Inventor: Greg Gustafson, Maple Plain, MN (US)

(73) Assignee: PENRAD TECHNOLOGIES, INC., Buffalo, MN (US)

( * ) Notice: Subject to any disclaimer, the term of this patent is extended or adjusted under 35 U.S.C. 154(b) by 415 days.

(21) Appl. No.: 12/625,926

(22) Filed: Nov. 25, 2009

(65) Prior Publication Data

US 2011/0125526 A1    May 26, 2011

Related U.S. Application Data

(60) Provisional application No. 61/282,000, filed on Nov. 24, 2009.

(51) Int. Cl.
| | |
|---|---|
| G06Q 50/00 | (2012.01) |
| G06F 19/00 | (2011.01) |
| G06Q 50/22 | (2012.01) |
| G06Q 50/24 | (2012.01) |
| G06T 7/00 | (2006.01) |
| G06T 7/40 | (2006.01) |

(52) U.S. Cl.
CPC .......... *G06F 19/3487* (2013.01); *G06F 19/321* (2013.01); *G06F 19/3443* (2013.01); *G06Q 50/22* (2013.01); *G06Q 50/24* (2013.01); *G06T 7/0012* (2013.01); *G06T 7/401* (2013.01); *G06T 2200/24* (2013.01); *G06T 2207/20104* (2013.01); *G06T 2207/30068* (2013.01)

(58) Field of Classification Search
CPC ................... G06T 2207/30068; G06F 19/321; G06F 19/3487
See application file for complete search history.

(56) References Cited

U.S. PATENT DOCUMENTS

| | | | |
|---|---|---|---|
| 4,972,264 A | 11/1990 | Bishop et al. | |
| 5,021,770 A | 6/1991 | Aisaka et al. | |
| 5,212,637 A | 5/1993 | Saxena | |
| 5,229,585 A | 7/1993 | Lemberger et al. | |
| 5,241,659 A | 8/1993 | Parulski et al. | |
| 5,321,520 A | 6/1994 | Inga et al. | |
| 5,325,478 A | 6/1994 | Shelton et al. | |

(Continued)

FOREIGN PATENT DOCUMENTS

| | | |
|---|---|---|
| EP | 0487110 A2 | 5/1992 |
| WO | WO 03/046796 A2 | 6/2003 |

(Continued)

OTHER PUBLICATIONS

Application and File History of U.S. Appl. No. 12/625,910, filed Nov. 25, 2009, Inventor Gustafson.

(Continued)

*Primary Examiner* — Luke Gilligan
(74) *Attorney, Agent, or Firm* — Patterson Thuente Pedersen, P.A.

(57) ABSTRACT

A system and method for analyzing and retrieving images of breast tissue abnormalities obtained from multiple sources. Providing a tool for a radiologist that includes a convenient region-of-interest association of mammogram, or other anatomical images, of an individual patient. One embodiment provides an efficient collection of all of the mammogram abnormalities for a patient. In yet another embodiment, the region-of-interest abnormalities in a single location in a patient's tissue are correlated across a variety of imaging modalities including X-rays, mammogram, CT, ultrasound, MRI, or other imaging technologies.

22 Claims, 9 Drawing Sheets

(56) References Cited

U.S. PATENT DOCUMENTS

| | | | |
|---|---|---|---|
| 5,343,390 A | 8/1994 | Doi et al. |
| 5,452,416 A | 9/1995 | Hilton et al. |
| 5,565,678 A | 10/1996 | Manian |
| 5,670,984 A | 9/1997 | Robertson et al. |
| 5,708,810 A | 1/1998 | Kern et al. |
| 5,719,567 A | 2/1998 | Norris |
| 5,917,929 A | 6/1999 | Marshall et al. |
| 5,940,188 A | 8/1999 | Kurozasa |
| 6,006,191 A | 12/1999 | DiRienzo |
| 6,047,257 A | 4/2000 | Dewaele |
| 6,176,429 B1 | 1/2001 | Reddersen et al. |
| 6,243,095 B1 | 6/2001 | Shile et al. |
| 6,246,782 B1 | 6/2001 | Shapiro et al. |
| 6,253,184 B1 | 6/2001 | Ruppert |
| 6,260,021 B1 | 7/2001 | Wong et al. |
| 6,311,419 B1 | 11/2001 | Inbar |
| 6,317,617 B1 | 11/2001 | Gilhuijs et al. |
| 6,347,241 B2 | 2/2002 | Burbank et al. |
| 6,347,299 B1 | 2/2002 | Holzman et al. |
| 6,349,143 B1 | 2/2002 | Hastings et al. |
| 6,355,024 B1 | 3/2002 | Small et al. |
| 6,434,262 B2 | 8/2002 | Wang |
| 6,587,830 B2 | 7/2003 | Singer |
| 6,614,921 B1 | 9/2003 | Chung et al. |
| 6,629,378 B2 | 10/2003 | Gustafson |
| 6,678,703 B2 | 1/2004 | Rothschild et al. |
| 6,766,297 B1 | 7/2004 | Lamer et al. |
| 6,785,358 B2 | 8/2004 | Johnson et al. |
| 6,831,648 B2 | 12/2004 | Mukherjee et al. |
| 6,901,156 B2 | 5/2005 | Giger et al. |
| 6,909,795 B2 | 6/2005 | Tecotzky et al. |
| 6,970,587 B1 | 11/2005 | Rogers |
| 7,081,976 B2 | 7/2006 | Harrington |
| 7,103,205 B2 | 9/2006 | Wang et al. |
| 7,124,760 B2 | 10/2006 | Wong |
| 7,146,031 B1 | 12/2006 | Hartman et al. |
| 7,184,582 B2 | 2/2007 | Giger et al. |
| 7,247,139 B2 | 7/2007 | Yudkovitch et al. |
| 7,308,126 B2 | 12/2007 | Rogers et al. |
| 7,321,668 B2 | 1/2008 | Horie et al. |
| 7,418,119 B2 | 8/2008 | Leichter et al. |
| 7,616,801 B2 | 11/2009 | Gkanatsios et al. |
| 7,668,718 B2 | 2/2010 | Kahn et al. |
| 7,783,094 B2 | 8/2010 | Collins et al. |
| 8,014,576 B2 | 9/2011 | Collins et al. |
| 8,014,578 B2 | 9/2011 | Suryanarayanan et al. |
| 8,391,574 B2 | 3/2013 | Collins et al. |
| 8,606,497 B2 | 12/2013 | Doherty et al. |
| 2001/0041991 A1 | 11/2001 | Segal et al. |
| 2001/0043742 A1 | 11/2001 | Melen |
| 2002/0016718 A1 | 2/2002 | Rothschild et al. |
| 2002/0070973 A1 | 6/2002 | Croley |
| 2002/0107885 A1 | 8/2002 | Brooks et al. |
| 2002/0139019 A1 | 10/2002 | Gustafson |
| 2002/0161628 A1 | 10/2002 | Lane Poor, Jr. et al. |
| 2003/0007598 A1 | 1/2003 | Wang et al. |
| 2003/0013951 A1* | 1/2003 | Stefanescu et al. ............ 600/407 |
| 2003/0026503 A1 | 2/2003 | Kallergi et al. |
| 2003/0065705 A1 | 4/2003 | Santos-Gomez |
| 2003/0103663 A1 | 6/2003 | Li et al. |
| 2003/0110178 A1 | 6/2003 | Woods et al. |
| 2003/0174873 A1 | 9/2003 | Giger et al. |
| 2004/0034550 A1 | 2/2004 | Menschik et al. |
| 2004/0052443 A1 | 3/2004 | Heaton et al. |
| 2004/0086158 A1* | 5/2004 | Leichter et al. ............... 382/128 |
| 2004/0101206 A1 | 5/2004 | Morimoto et al. |
| 2004/0111299 A1 | 6/2004 | Onishi |
| 2004/0122702 A1* | 6/2004 | Sabol et al. ........................ 705/2 |
| 2004/0141661 A1 | 7/2004 | Hanna et al. |
| 2004/0181412 A1 | 9/2004 | Menhardt |
| 2004/0258287 A1 | 12/2004 | Gustafson |
| 2004/0258291 A1 | 12/2004 | Gustafson |
| 2005/0031177 A1 | 2/2005 | Langille et al. |
| 2005/0049497 A1 | 3/2005 | Krishnan et al. |
| 2005/0108060 A1 | 5/2005 | Sasano |
| 2005/0123185 A1 | 6/2005 | Balasubramanian et al. |
| 2005/0149360 A1 | 7/2005 | Galperin |
| 2005/0171430 A1 | 8/2005 | Zhang et al. |
| 2005/0177312 A1 | 8/2005 | Guerrant et al. |
| 2005/0216314 A1 | 9/2005 | Secor |
| 2005/0238216 A1 | 10/2005 | Yoden |
| 2005/0244041 A1 | 11/2005 | Tecotzky et al. |
| 2005/0244082 A1 | 11/2005 | Yamatake |
| 2006/0058603 A1 | 3/2006 | Dave et al. |
| 2006/0111937 A1 | 5/2006 | Yarger et al. |
| 2006/0147099 A1 | 7/2006 | Marshall et al. |
| 2006/0173303 A1* | 8/2006 | Yu et al. ........................ 600/437 |
| 2006/0212317 A1 | 9/2006 | Hahn et al. |
| 2006/0257009 A1 | 11/2006 | Wang et al. |
| 2006/0274928 A1* | 12/2006 | Collins et al. ................. 382/132 |
| 2007/0003119 A1 | 1/2007 | Roehrig et al. |
| 2007/0038085 A1 | 2/2007 | Zhang et al. |
| 2007/0041623 A1 | 2/2007 | Roehrig et al. |
| 2007/0098243 A1 | 5/2007 | Gustafson |
| 2007/0118384 A1 | 5/2007 | Gustafson |
| 2007/0118399 A1* | 5/2007 | Avinash et al. .................... 705/2 |
| 2007/0122021 A1 | 5/2007 | Zingaretti et al. |
| 2007/0185732 A1 | 8/2007 | Hicks et al. |
| 2007/0211930 A1 | 9/2007 | Dolwick et al. |
| 2007/0274585 A1 | 11/2007 | Zhang et al. |
| 2008/0019581 A1 | 1/2008 | Gkanatsios et al. |
| 2008/0025592 A1 | 1/2008 | Jerebko et al. |
| 2008/0130968 A1 | 6/2008 | Daw et al. |
| 2008/0162352 A1 | 7/2008 | Gizewski |
| 2008/0187241 A1* | 8/2008 | Talati et al. .................... 382/282 |
| 2008/0255849 A9 | 10/2008 | Gustafson |
| 2008/0267470 A1 | 10/2008 | Zhang et al. |
| 2008/0285825 A1 | 11/2008 | Zhang et al. |
| 2009/0093711 A1 | 4/2009 | Hermosillo Valadez |
| 2009/0129644 A1* | 5/2009 | Daw et al. ...................... 382/128 |
| 2009/0154782 A1 | 6/2009 | Zhang et al. |
| 2009/0165009 A1 | 6/2009 | Heffernan et al. |
| 2009/0171236 A1* | 7/2009 | Davies .......................... 600/547 |
| 2009/0171871 A1 | 7/2009 | Zhang et al. |
| 2009/0185732 A1 | 7/2009 | Zhang et al. |
| 2009/0192823 A1 | 7/2009 | Hawkins et al. |
| 2009/0220138 A1 | 9/2009 | Zhang et al. |
| 2009/0238421 A1 | 9/2009 | Zhang et al. |
| 2009/0238422 A1 | 9/2009 | Zhang et al. |
| 2009/0310843 A1 | 12/2009 | Moriya |
| 2010/0086185 A1 | 4/2010 | Weiss |
| 2010/0280375 A1 | 11/2010 | Zhang et al. |
| 2011/0028825 A1* | 2/2011 | Douglas et al. ............... 600/407 |
| 2011/0087137 A1 | 4/2011 | Hanoun |
| 2011/0110576 A1* | 5/2011 | Kreeger et al. ................ 382/132 |
| 2011/0123079 A1 | 5/2011 | Gustafson |
| 2011/0137132 A1 | 6/2011 | Gustafson |
| 2012/0029936 A1 | 2/2012 | Hanoun |
| 2013/0016092 A1 | 1/2013 | Collins et al. |
| 2013/0343626 A1 | 12/2013 | Rico et al. |

FOREIGN PATENT DOCUMENTS

| | | | |
|---|---|---|---|
| WO | WO 03/046796 A3 | 6/2003 |
| WO | WO 2005/003912 A2 | 1/2005 |
| WO | WO 2005/003912 A3 | 1/2005 |

OTHER PUBLICATIONS

Application and File History of U.S. Appl. No. 12/625,898, filed Nov. 25, 2009, Inventor Gustafson.

Application and File History of U.S. Appl. No. 10/418,191, filed Apr. 17, 2003, Inventors Schafer et al.

Henry A. Swett, Pradeep G. Mutalik, Vladimir P. Neklesa, Laura Horvath, Carol Lee, Joan Richter, Irena Tocino, and Paul R. Fischer, Voice-Activated Retrieval of Mammography Reference Images, Journal of Digital Imaging, vol. 11, No. 2 May 1998: pp. 65-73.

GPCALMA: a Grid-based tool for Mammographic Screening. Authors: S. Bagnasco, U. Bottigli, P. Cerello, S.C. Cheran, P. Delogu, M.E. Fantacci, F. Fauci, G. Forni, A. Lauria, E. Lopez Torres, R. Magro, G.L. Masala, P. Oliva, R. Palmiero, L. Ramello, G. Raso, A. Retico, M. Sitta, S. Stumbo, S. Tangaro, E. Zanon. HealthGrid Workshop 2004. arXiv.org.

(56) References Cited

OTHER PUBLICATIONS

Selenia—User Guide / Administrator Guide, P/N 9-500-0293, Rev. 1, Copyright 2002-2003.
Application and File History of U.S. Appl. No. 11/443,742, filed May 31, 2006, Inventor Gustafson.
Application and File History of U.S. Appl. No. 11/603,554, filed Nov. 22, 2006, Inventor Gustafson.
Application and File History of U.S. Appl. No. 10/871,763, filed Jun. 17, 2004, Inventor Gustafson.
Application and File History of U.S. Appl. No. 10/871,740, Jun. 17, 2004, Inventor Gustafson.
PenRad, "Technologist Mammography System Handbook", Copyright 1995-2003 rev. Jul. 7, 2003.
AuntMinnie, "Confirma, PenRad Steamline Breast MRI Reporting". Nov. 27, 2007.
PenRad, "PenRad CAD Connectivity Module" Copyright 1997-2003 rev. Jul. 2, 2003.
AuntMinnie, "A Guide to Digital and Soft-Copy Mammography" Jul. 21, 2005.
Altera, "Medical Imaging Implementation Using FPGAs" Apr. 2006.
AuntMinnie, "PenRad Highlights Mammography Management Tools" Nov. 7, 2005.
PenRad, "PenRad Mammography Information System".Copyright Sep. 18, 2002 rev. Jun. 16, 2004.
Internet Archive-PenRad.pdf files, as downloaded on Apr. 24, 2012.
Application and File History for U.S. Appl. No. 12/953,100, filed Nov. 23, 2010, inventor Gustafson.
Hsu et al.,"SPIRS: A Web-based Image Retrieval System for Large Biomedical Databases", 21 pages. Sep. 26, 2009.
PenRad, Mammography Information System awith R2 Checkmate Ultra CAD Connectivity Module. Copyright Sep. 18, 2002—REV. Jun. 16, 2004.
Definition of "Synthesize" freedictionary.com as download Oct. 22, 2012.
Doi, "Current Status and future potential of computer-aided diagnosis in medical imaging" The British Journal of Radiology, 78. 2005.

\* cited by examiner

Right Breast Mammogram Abnormality Detailing : Christine Jade Anderson, 11/18/2009 20:34:32
Joanne W. Adamsick  DOB: 09/01/1926  AGE: 83  F  PID: 102828  SSN: 987654321

Ab Type
- Seen/US only
- Possible
- Multiple
- Cluster of
- Various

Profile Ab
- Mass
- Mass solid
- Mass part solid
- Mass skin

Shape
- Irregular
- Lobulated
- Oval
- Reniform
- Round

Margin
- Circumscribed
- Indistinct
- Microlobulated
- Obscured
- Spiculated

Density
- High density
- Low density
- Equal density
- Fat containing
- Cent lucent

Assoc Calc
- Generic calcs
- Amorphous
- Branching
- Coarse
- Dystrophic
- Eggshell
- Fine
- Heterogeneous
- Indistinct
- Large rodlike
- Layering
- Linear
- Lucent centered
- Milk of calcium
- Pleomorphic
- Punctate
- Rim
- Round
- Skin
- Spherical
- Suture
- Vascular

Calc Dist
- Clustered
- Diffuse
- Grouped
- Linear
- Regional
- Scattered
- Segmental

Assoc Findings
- Archit distortion  Post surgical so
- Axillary adenop  Skin involvemen
- Brachy tube  Seroma
- Bx clip  Skin lesion
- Bx clips  Skin retraction
- Chest wall inva  Skin thicken
- Gold Seed  Surgical clip
- Nipple retract  Surgical clips
- Hematoma  Trab thicken

Corresponds with
- US          sz <US     sz > US
- MRI         sz <MRI    sz > MRI
- Palpated    sz <palp   sz > palp
- Pain        Tender     Incidental
- Sc'tim      Ductog.    Pst-op chg
- Redness     Concern    Skin marke

Not Prev Seen On
- Clinical exam MRI
- Mammogram Ductogram
- Ultrasound

Special Circumstances

Addl Views | Dem By Prior
- Confirm | Ultrasound
- Do not Confirm | Aspiration
-  | Biopsy
-  | MRI

- Not sig If not palpable
- Not on prev study
- Visible ML only

Consistent with
- Likely represents
- Most likely
- Resembles
- w/ differential dia
- Abscess
- Carcinoma
- Carcinoma know
- Cluster of cysts
- Cyst
- Cyst Oil
- DCIS
- Fat necrosis
- Fibroadenoma
- Fibroad. degener.
- Fibrocystic chang
- Fibroglandular tis
- Fibrosis
- Hamartoma
- Hematoma
- Intramam node
- Lipoma
- Lymph node.
- Mass Solid
- Mastitis
- Papillary lesion
- Post surg scar
- Post lumpec scar
- Prev biopsy
- Prev surgery
- Prev trauma
- Radical scar
- Seroma
- Skin lesion

Impression & Recs
- <charge birads>
- [5 Highly suggestive
- Unless previous sho
- Ultrasound
- Poss. Ultrasound
- Biopsy
- BX base on clinical
- Clinical correlation
- Diagnostic aspiration
- FNA biopsy
- MRI
- MRI Biopsy
- Needle loc. & surg b
- US loc. & surg bx
- Poss. core bx
- Poss. stereo vac bx
- Poss. US bx
- Scintimammography
- Stereotactic core bx
- Surgical Consult
- Surgical consult & bx
- Ultrasound guided b
- Vacuum Bx

Changes
- New
- Not sig chg.
- Stable
- No long seen
- Part removed
- Incr in size
- Decr in size
- Less prom.
- More prom.
- Incr in number
- Decr in number
- Incr in calcs
- Decr in calcs

Size/Dist/Axis
- Ab dimensions>
- Titles on report
- Parallel/skin
- Perpendic/skin
- In skin
- In mammary
- Hide clock on rpt
- Hide location
- Use in/out/up/lo Add Text | OK | Cancel | Help | Set Def m2:b2:t121
m32:b8:t180

402, 404, 406, 408, 410, 412, 414, 416, 400

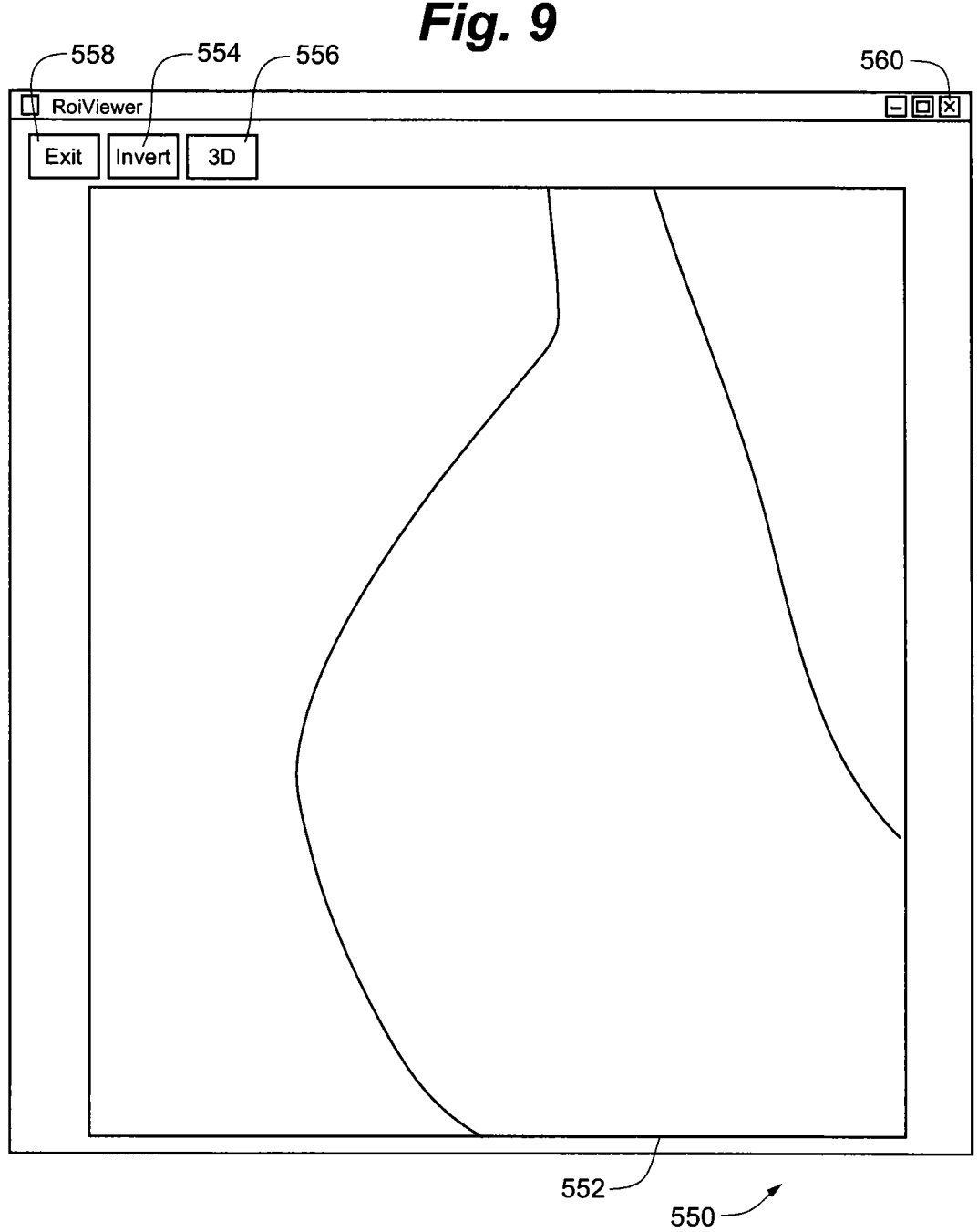

MULTIPLE MODALITY MAMMOGRAPHY IMAGE GALLERY AND CLIPPING SYSTEM

RELATED APPLICATIONS

This application claims the benefit of U.S. Provisional Application No. 61/282,000, entitled "MAMMOGRAPHY INFORMATION SYSTEM" and filed on Nov. 24, 2009, which is incorporated herein by reference in its entirety.

The following co-pending patent applications of common assignee contain some common disclosure: "Mammography Statistical Diagnostic Profiler and Prediction System," and "Mammography Information System," filed Nov. 25, 2009, having Ser. Nos. 12/625,910 and 12/625,898, respectively, which are incorporated herein by reference in their entireties. A copy of each of the above-identified related applications is attached hereto as Appendix A and Appendix B, respectively.

TECHNICAL FIELD

The invention relates to data management of medical data and more specifically to the selection, association, and storage of multiple patients' diagnostic images acquired by imaging systems of various types in a database.

BACKGROUND OF THE INVENTION

Historically, interpretation and diagnosis of mammograms and other medical image analysis has been performed using hardcopy x-ray films viewed on an alternator that typically allows x-ray films to be illuminated and masked for diagnostic viewing. Newer technology allows a radiologist or other medical professional to view mammograms and other diagnostic images electronically on high-resolution monitors. These images can also be digitally stored and transmitted across secure networks for archiving or review by other professionals.

A radiologist generally begins his or her review process by reviewing a patient's background information relevant to a radiology study, such as a patient's name, age, and any applicable medical conditions or risk factors. After reviewing the background information, the radiologist views multiple images created by radiological, X-ray, computed tomography (CT), ultrasound, magnetic resonance imaging (MRI), tomosynthesis, or other imaging technique of the patient's breast, or other organ, and dictates or uses a computerized information system to track findings, create reports, and make recommendations for future examinations. Such findings can include information pertaining to tissue density, the presence of masses, cysts, calcifications and other abnormalities, or any other breast tissue characteristics.

While there has been recent debate regarding the frequency at which women should undergo regular mammogram screenings, and at what age such screenings should begin, it is unlikely that the relatively quick and typically effective practice of mammography screening for breast cancer will disappear completely. Accordingly, there will continue to be a need for radiologists to view and interpret the images generated from patient examinations and screenings. Because the risk of breast cancer threatens the lives of many women, especially those over age 40, radiologists are often inundated with large numbers of mammogram images that must be viewed and, if abnormalities are present, categorized in order to determine if further examination is required. The developments in advanced patient imaging techniques, such as MRI, are also increasing the raw number of images that a radiologist can review. Therefore, there is an ongoing need to improve the speed and efficiency of the radiologist's review of the mammogram images, without sacrificing accuracy, and with the smallest number of false-positive diagnoses. Additionally, given that mammograms are taken periodically, such as annually or biannually, once screening begins for a particular woman, there is also a need to manage, track and analyze data taken over a period of years or decades for a woman.

One commercially available computerized mammography information system (MIS) in use by radiologists to review patient images is the PenRad Mammography Information System, which is able to electronically track abnormalities, generate statistics, and provide patient correspondence. The PenRad™ system is described in copending U.S. patent application Ser. Nos. 12/625,910 and 12/625,898, each filed on Nov. 25, 2009, and incorporated by reference in their entireties, and is available from PenRad. This system provides for the digital correlation of patient data related to a mammography or other diagnostic imaging procedure.

Legislation has mandated that mammography facilities track positive mammography findings and correlate such findings with biopsy results, maintain statistics for mammography medical outcome and analysis audits on each physician, and provide direct written notification to all patients of their exam results. The generation and correlation of this data is maintained locally by each medical center for each patient.

One system for categorizing this information is the Breast Imaging-Reporting and Data System (BI-RADS) published by the American College of Radiology (ACR). BI-RADS provides a system of mammography assessment categories in the form of standardized codes assigned by a radiologist during or after the viewing and interpretation of a medical image. BI-RADS allows for concise and unambiguous understanding of patient records between multiple radiologists and medical facilities. Consequently, a large number of mammogram images, biopsy results, and diagnosis statistics are potentially available in a patient-anonymous format, in compliance with the Health Insurance Portability and Accountability Act of 1996 (HIPAA).

Recently, Digital Imaging and Communications in Medicine (DICOM) systems have become the accepted format for medical imaging systems. This format provides for the distribution and viewing of medical studies and images across a variety of platforms. The use of DICOM has, among other things, enabled industry compatibility and improved workflow efficiency between imaging and other information systems located in various healthcare environments. Currently, the DICOM standard is an 18-part publication, PS 3.1-2008 through PS 3.18-2008 describing a standard for digital imaging and communications in medicine developed by the American College of Radiology (ACR) and the National Electrical Manufacturers Association (NEMA) which is hereby incorporated by reference in its entirety. Among other elements, the DICOM standard provides a method of uniquely numbering any image or other information object to facilitate the unambiguous identification of images or information objects as they are viewed or manipulated in a system or transported across a network.

SUMMARY OF THE INVENTION

Embodiments of the invention relate to systems and methods for analyzing and retrieving patient abnormality data for use with a mammography information system as part of or in conjunction with the diagnosis and interpretation of patient mammography images that substantially meets the aforementioned needs of the medical industry.

In an embodiment, a method for managing patient mammography data comprises obtaining a first mammographic image, wherein the image includes a region of interest categorized according to an established lexicon, storing a selected region of the first mammographic image as a second image, mapping the second image to a storage location of the first mammographic image, and associating the selected region with the categorized region of interest.

In an embodiment, a configurable mammography diagnostic system comprises a plurality of electronic displays, at least one of the plurality of electronic displays configured to display a mammographic image having at least one region of interest, a graphical user interface configured to be displayed on at least one of the plurality of electronic displays and comprising an anatomical diagram on which the at least one region of interest can be marked, a clipping tool with which a portion of the mammographic image including the at least one region of interest and displayed on at least one of the plurality of electronic displays can be selected as a second image, the second image displayable on at least one of the plurality of electronic displays as a subset of the mammographic image, and a processing engine configured to link the second image to the mammographic image, store the second image in an image database, and to associate the second image with a corresponding region of interest marked on the anatomical diagram.

In an embodiment, a method of correlating multiple image modalities comprises obtaining a first mammographic image including a region of interest categorized according to an established lexicon, obtaining a second mammographic image, wherein the second mammographic image is of a different modality than the first mammographic image, storing a selected region of the first mammographic image as a second image, storing a selected region of the second mammographic image as a third image, associating the second image with an anatomical diagram, associating the third image with the anatomical diagram, associating the second image with the categorization of the region of interest, associating the third image with the categorization of the region of interest, and presenting the second image and the third image in a gallery based on a selection of the region of interest.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The embodiments of the present invention may be more completely understood in consideration of the following detailed description of various embodiments in connection with the accompanying drawings, in which:

FIG. 2 is an example of a mammography exam data-form suitable for use with embodiments of the disclosed invention.

FIG. 6 is another example of an embodiment of a ROI data form for use with embodiments of this invention.

FIG. 9 is an example embodiment of a ROI viewer depicting an individual image for use with embodiments of this invention.

Figure 1:
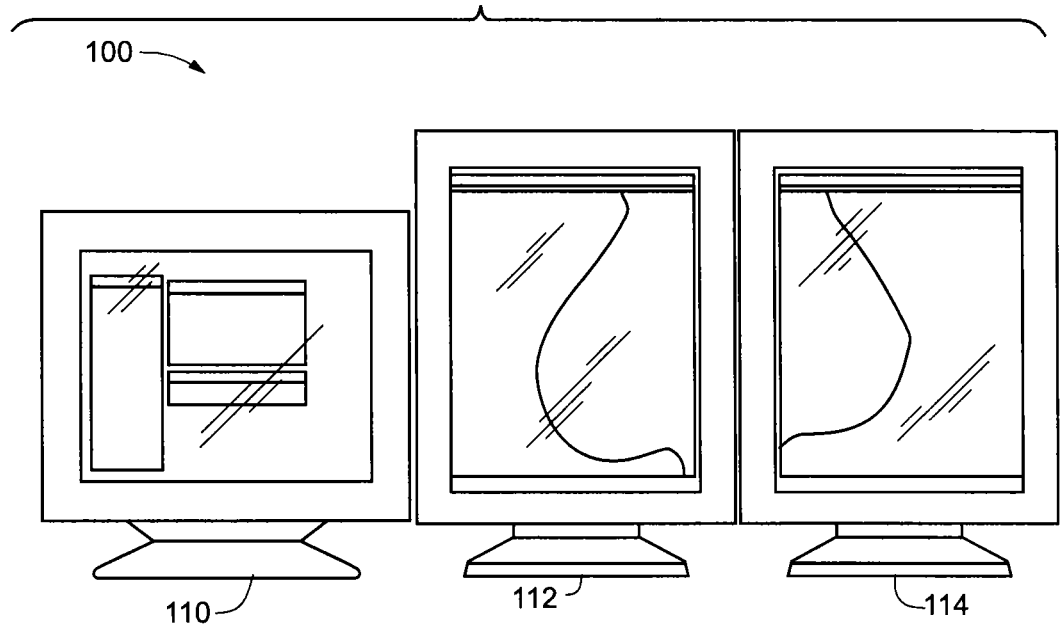
FIG. 1 is an example of a mammogram information system (MIS) display workstation according an embodiment of the invention.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention as defined by the appended claims.

DETAILED DESCRIPTION OF THE DRAWINGS

The increasing availability and quantity of digital information representing patient medical data and diagnostic images has created a need for a system that allows a doctor or radiologist to quickly review, organize, and if necessary retrieve, multiple diagnostic images that may be indicative of an individual patient's condition. In addition to the availability of digital mammography images, other patient associated data, such as biopsy or other test results and even entire medical histories or correspondence records can be stored in a digital format. Therefore, there is a need for a system that will quickly allow a radiologist to select a ROI in a mammogram or other image and correlate the ROI to a mapping or outline of the patient's anatomy in order to improve efficiency of patient diagnosis and record retrieval including a mechanism to "clip" a ROI from any image modality, or form of electronic record, and associating that "clipping" with a specific ROI placement in the patient's record.

In an example embodiment, a MIS is provided for use by a radiologist or other medical professional that preloads all of an individual patient's medical images for a specific portion of the patient's anatomy, regardless of the modality used to create the images. For example, in a breast cancer screening, any available x-ray, ultrasound, MRI, biopsy, or other images for the patient are retrieved and preprocessed by an appropriate CAD algorithm. A CAD module for the appropriate image type can isolate one or more ROI for review in an individual image. The disclosed invention takes these individual CAD results and correlates any common ROI findings between images of the same or different modalities. A summary "map" or outline of the examined patient's anatomy is then generated and displayed for the medical professional along with any other details about the potential ROI(s) that were generated by the CAD module(s).

The mammography image gallery and clipping system according to the present invention provides a convenient organization of all of the images associated with a ROI, regardless of modality, for presentation to a medical professional. The system stores lower resolution clippings, or thumbnail images, for pathological images, reports, and abnormalities found and optionally categorized, by radiologists or CAD products at a facility that have been entered into a mammography information system. The system stores low resolution images as well as the reference to the original image and ROI of the original image. As more patients are definitively diagnosed and their pathology records updated in the system, the larger the collection of abnormality images depicting a previously diagnosed and imaged condition that become available in the system. This system can be integrated into an existing MIS or utilized as a standalone interface providing access to a large sample of mammogram abnormality images.

The system also provides an efficient mechanism for creating a comprehensive collection of abnormality data. The collection comprising a uniform lexicon of classifications that allows for further analysis and study of the data while still maintaining patient privacy as required by the applicable law. Those skilled in the art of developing and maintaining electronic databases will appreciate and understand the tradeoffs associated with the storage requirements necessary for the implementation of the contemplated system. As numerous mammography facilities implement this non-patient identifying (and HIPAA compliant) data can be transferred to a central location accumulating a more complete database of abnormality images and the corresponding characterization of data points for various pathology types.

The invention can be better understood by reference to FIGS. 1-9. FIG. 1 illustrates an example embodiment of a mammogram display workstation 100. A typical mammogram display workstation 100 includes a controller display system 110 and at least one high-resolution image monitor 112. One or more additional high-resolution image monitor units 114 can also be used to provide additional viewing area to provide for the comparison of two or more images at full resolution. The controller display system 110 is any of a variety of commonly available video display monitors coupled to a personal computer such as an IBM-PC or compatible system running a version of the Microsoft WINDOWS operating system, or the equivalent thereof. In an embodiment, the image monitors 112 and 114 are liquid crystal displays (LCDs) that provide high-resolution and enhanced contrast for ease of viewing images, but may also be a cathode ray tube or other appropriate display in other embodiments. An exemplary image monitor can display approximately 2500×2000 pixels, although a variety of image monitor sizes are contemplated. In one embodiment, the mammogram display workstation 100 includes a server computer (not shown) that runs DICOM communications components of the mammogram display workstation 100; alternatively, this DICOM software may run on the controller display system 110. In yet another embodiment, a server computer is included that runs an Archived Image Retrieval service; alternatively, this software may also run on the controller display system 110 or on the DICOM compliant server.

Figure 2:
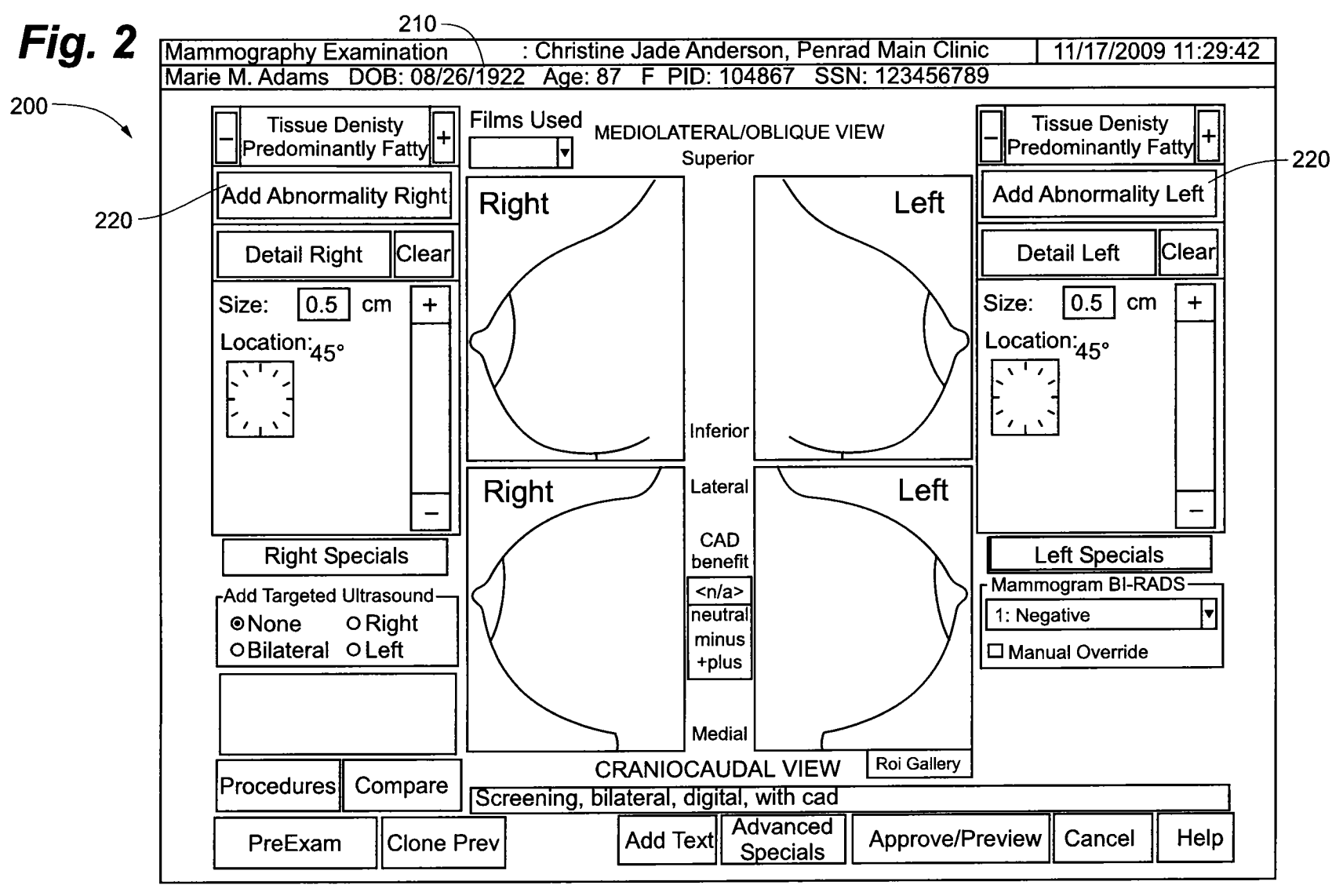

FIG. 2 illustrates an example embodiment of a medical diagnostic system that includes an abnormality-summary window 200. Abnormality-summary window 200 provides a convenient patient information summary 210 and an interface to import or enter additional data. In window 200 the radiologist can enter abnormality data for either the left or right breast by clicking on an "Add Abnormality" button 220. Additionally, a user can import a CAD report detailing any abnormalities that have been detected by existing CAD software. Examples of suitable CAD software include the CadStream product by Confirma and the B-CAD product by Medipattern.

Figure 3:
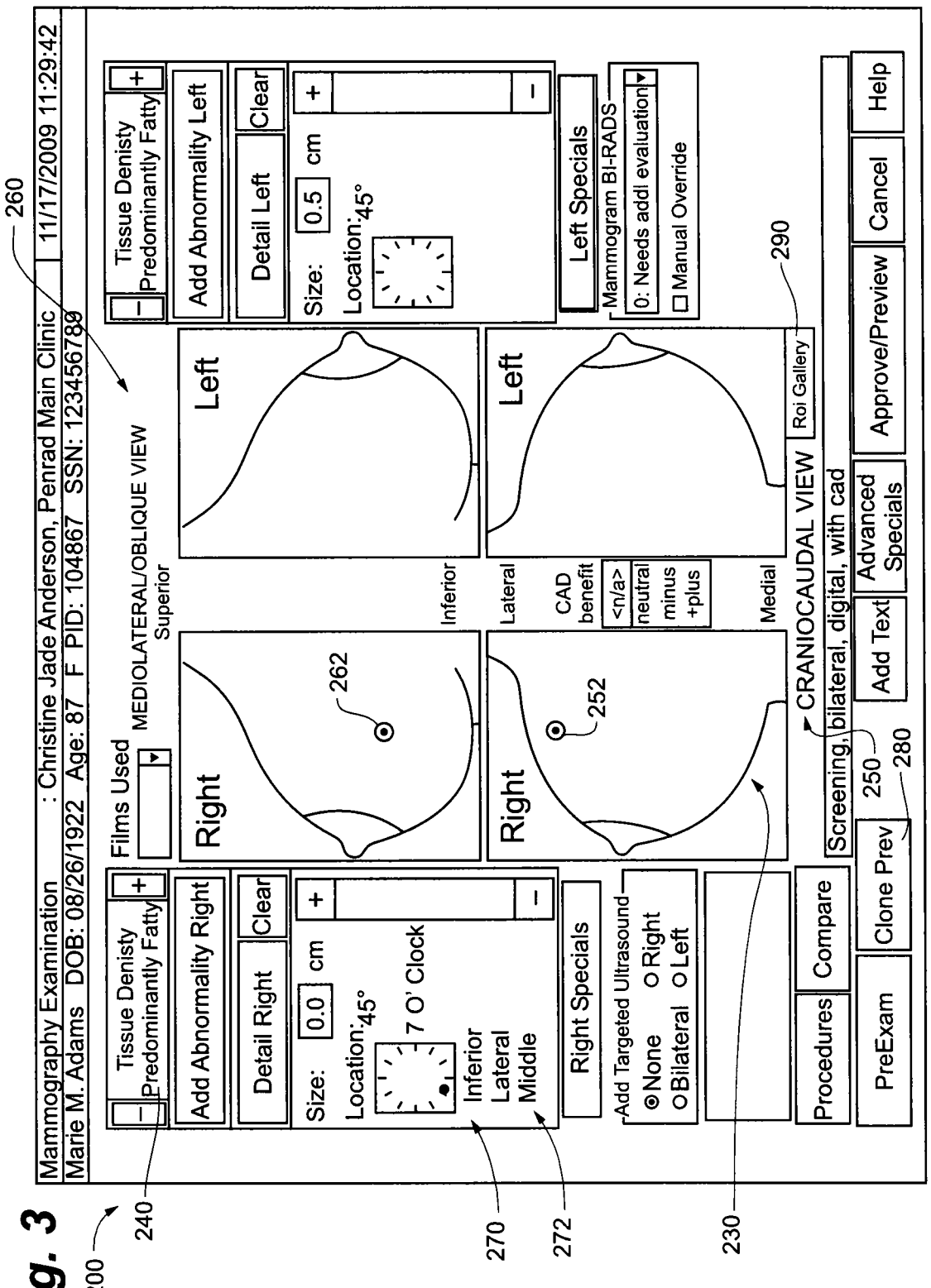
FIG. 3 is an example of the mammography exam data-form of FIG. 2 indicating a region of interest (ROI).

As shown in FIG. 3, imported CAD information stored in compliance with a pre-determined system such as BI-RADS is used to generate a wire-frame map or guide 230 depicting the location and depth of a ROI in or on a patient's anatomy that was detected by the CAD software or entered manually by a radiologist. The density of the patient's tissue is also presented in selector 240. The guide 230 includes both a craniocaudal (CC) view 250 and a mediolateral/oblique (ML) view 260 of both the left and right breasts of a patient. The ROI is depicted by the craniocaudal mark 252 and the mediolateral mark 262. In other situations, an abnormality may only be visible in one or the other of the ML or the CC view and, accordingly, only a single mark would be displayed in either the craniocaudal (CC) view 250 or the mediolateral/oblique (ML) view 260.

In an embodiment, the ROI data underlying either craniocaudal mark 252 or mediolateral mark 262 can be represented as the number of pixel spaces from at least two edges of the original image represented by the ROI. The retention of the number of pixels from at least two edges provides for the derivation of the location of the ROI on the original image. This allows the storage of multiple ROI for a single high-resolution image without the need to store multiple copies of the high-resolution image or even high-resolution clippings. It also permits derivation or mapping of an ROI in one image to other images based on known pixel sizes and edge distances.

In another alternative embodiment, the data underlying these two marks are used to then calculate an approximate location of the abnormality as viewed by a physician when facing the patient. This calculation also compensates for the fact that during the creation of a mammography image, the patient's breast is compressed to increase the amount of viewable tissue in the two-dimensional x-ray image. Additionally, compensation must be made for the angle at which the mediolateral/oblique view 260 is taken relative to the craniocaudal view 250 during mammogram imaging. Those skilled in the art will appreciate that the two views are not necessarily created at angles exactly perpendicular to each other due to the wide variety of patient anatomy and the need to capture as much tissue as possible in each image. The resulting combination of the craniocaudal data and the mediolateral data produce the clock-position 270 as shown for the exemplary ROI. This calculation is not possible if the ROI is only visible on a single image, as both a craniocaudal and mediolateral position are required, along with a distance either from the patient's nipple or chest wall to calculate the location of the ROI in three-dimensional space.

An abnormality does not need to be located or seen in both views to be characterized. Often in mammography an abnormality is only seen in one view and additional imaging is conducted to confirm its location in another view. The additional imaging can also reveal superimposed tissue, a situation in which the breast tissue of several layers was compressed together causing a potential mass seen in a single image with the appearance of an actual abnormality. A radiologist viewing multiple images of the same tissue area can appropriately categorize these situations.

Also shown in FIG. 3 is a three-word indication 272 of the location of the ROI in the patient's breast. In this example the ROI is located in the inferior (lower), lateral (outside), middle (distance between the chest and nipple) portion of the patient's right breast. Similar terms for the remaining quadrants and depth are provided by the ACR guidelines and will be understood by those skilled in the art.

An additional feature of the system is the capability of importing any ROI from a patient's previous examination that are already present in the system's database. A radiologist or technician can select the "Clone Prey" button 280 to review and import data from a previous examination. This feature further eliminates the need for duplicated effort on the part of the medical professional conducting the review of the patient's exam images.

Figure 4:
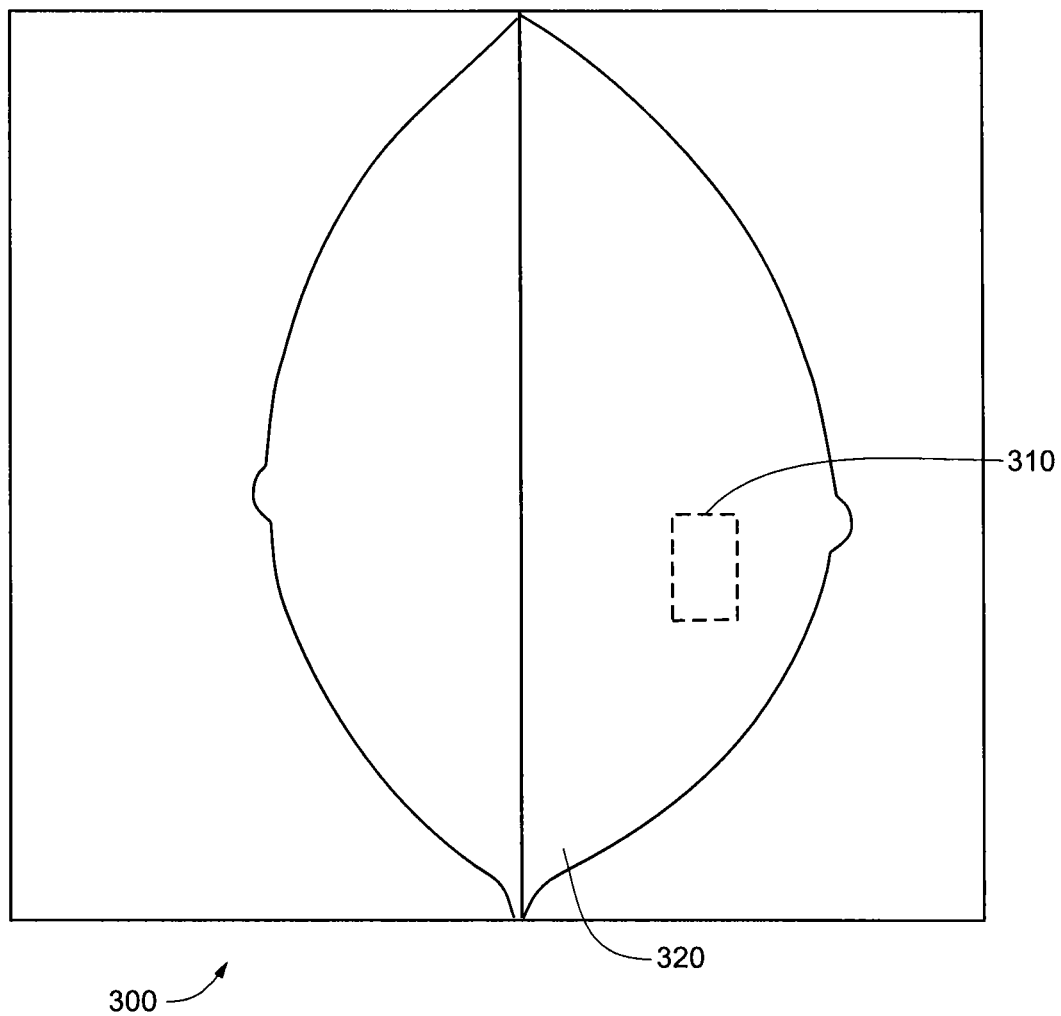
FIG. 4 is an example of a mammogram image with an ROI indicated.
Figure 5:
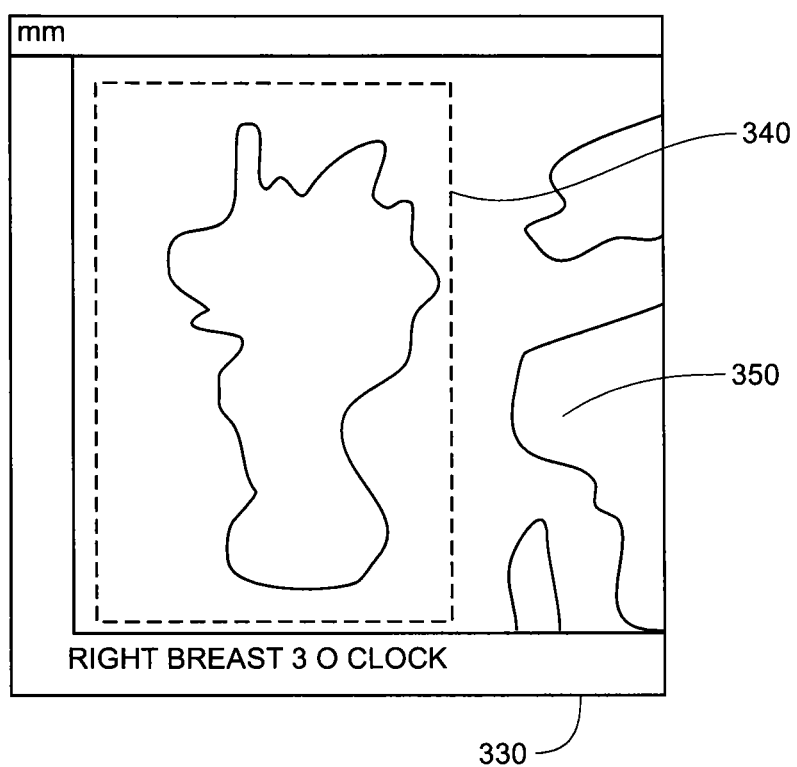
FIG. 5 is an example of an ultrasound image with an ROI indicated.

The system is capable of handling a variety of imaging technologies. FIG. 4 depicts an exemplary x-ray generated mammogram image 300 with an ROI indicated by a dashed outline 310 on the image 300 of the patient's breast tissue 320. FIG. 5 depicts an exemplary ultrasound image 330 with an ROI indicated by a dashed outline 340 on the image 330 of the patient's breast tissue 350. While the type of information depicted in a mammogram image 300 is clearly different from the ultrasound image 330, the system maintains the ROI indicated on each respective image by storing the coordinates of each ROI as an offset, in one embodiment the number of pixels, from at least two edges of the original digital image, regardless of the technique employed to generate the image. These coordinates are then used to calculate the distance from the patient's chest wall, nipple, or other appropriate reference point, to determine the measurements defining the location of the ROI. Similar techniques can be applied to other imaging technologies such as MRI or CT images that are capable of being stored in a standardized digital format where the correlation of the number of pixels in the image to the real-world distance depicted in the image is known.

FIG. 6 depicts an embodiment of an abnormality detailing-window 400. The detailing window 400 provides an interface for a radiologist to enter or view the detailed attributes that describe an abnormality in a selected ROI. FIG. 6 depicts the attribute of abnormality type 402 as with "Mass" 404 being selected to describe the ROI depicted in FIG. 3. FIG. 6 also depicts the selection of three additional characteristics that describe the ROI. The ROI is characterized as "Irregular" 406 in shape, having a "Microlobulated" 408 margin, and having a "High density" 410. In the "Impression & Recs" area 412 the addition of the "5 Highly suggestive" 414 attribute indicates that a follow-up examination of the patient is necessary. In this case, the radiologist has selected the "Ultrasound guided bx" option 416, indicating that the recommended next step for the patient is an ultrasound-guided biopsy of the abnormality. As shown in FIG. 6, additional details related to the image characterization or the patient examination can also be entered into the system.

Detailing window 400 displays information that can be stored as BI-RADS compatible data points, or another suitable lexicon. Optionally the ROI data can be generated by a CAD software package used to pre-evaluate and categorize the ROI in the MIS. In one embodiment, the CAD software package can populate the various fields presented by an abnormality window, such as exemplary MRI abnormality-dimensioning window 442. Detailing window 400 also provides a radiologist with an interface to adjust, re-characterize, correct, add, or remove the ROI data based on their professional assessment of the ROI depicted in the patient's images if they radiologist disagrees with the CAD generated results. All of this information can be stored in a database configured to correlate all of a patent's ROI data and images.

The features provided by the system can also be combined with any one of several available computer aided diagnostic (CAD) products to validate, improve, and allow simplified characterization of images. A CAD product can be integrated to provide the lexicon abnormality descriptors to generate ROI entries, such as those depicted in FIG. 6. The CAD product can pre-select the ROI classifications for each abnormality detected. This combination is especially advantageous as it reduces the number of radiologist provided entries to only corrections to the CAD interpretation of an ROI or any ROI that were not categorized initially by the CAD product. While a handful of mouse clicks or keyboard entries, or similar gestures, may seem trivial the combined time savings over the high volume of patient images that must be reviewed can yield a substantial savings in time, cost and comfort.

The combination of the database of ROI characterizations and the ROI images allows an embodiment of the system to provide a radiologist with images stored at a local facility for comparative diagnostic purposes. The system also allows a radiologist to select images based on the BI-RADS or other lexicon abnormality descriptors, allowing a comparison of additional images from a larger database or final pathology results if the abnormality was biopsied.

Figure 7:
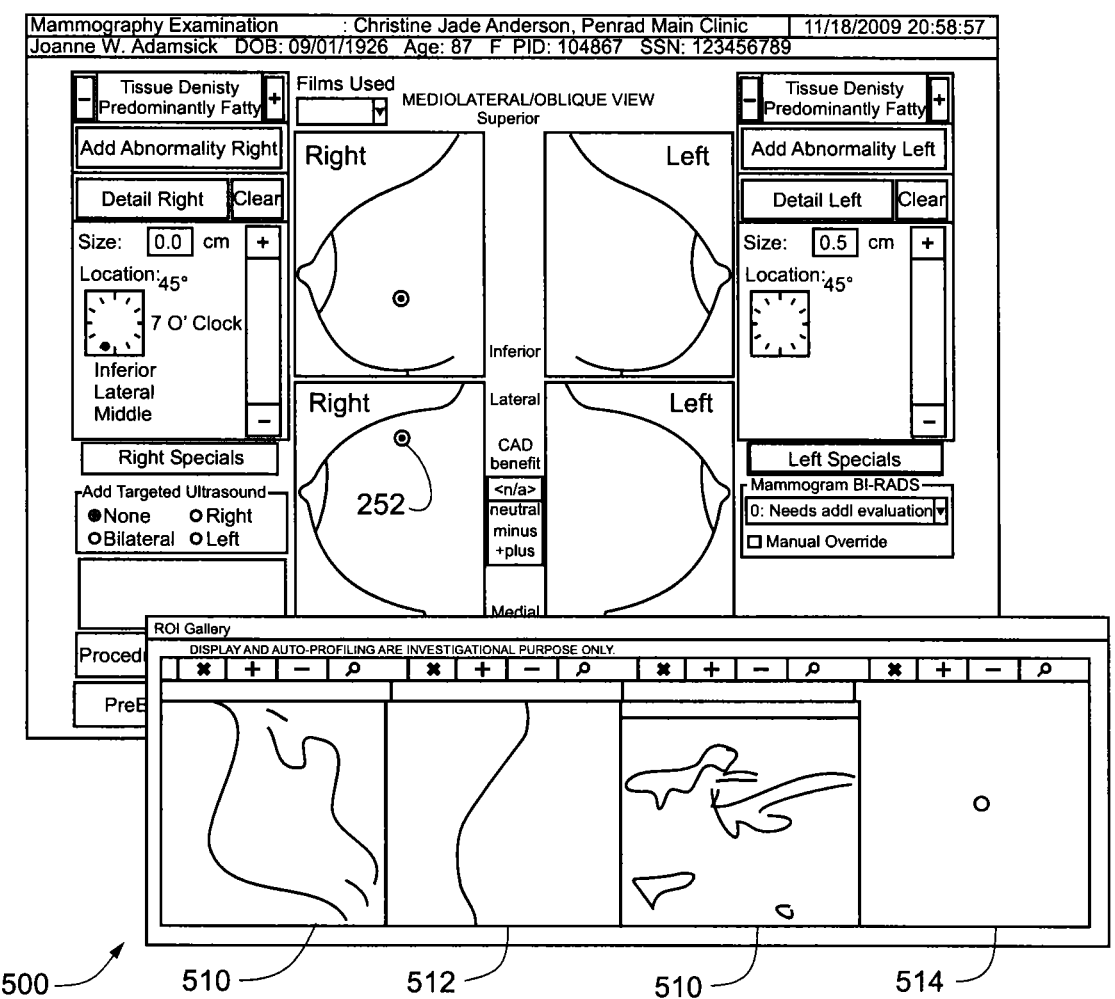
FIG. 7 is an example of a mammography exam data-form and an example of a ROI gallery window.

FIG. 7 depicts an embodiment of a ROI Gallery 500 containing selected image clippings 510 that have been associated with the ROI depicted by the craniocaudal mark 252. The activation of the "Roi Gallery" button 290, shown in FIG. 3, causes the ROI Gallery 500 to be presented to the user. The image clippings 510 can be selected from any region of a medical image available to the radiologist on the MIS. A low magnification image 512 can be useful to identify a large area of tissue. Alternatively, a smaller, higher magnification image 514 can provide the radiologist with greater detail.

The association of image clippings 510 can allow the radiologist to associate a variety of images with the set of categories, such as those associated with the ROI of FIG. 3. By correlating a subset of a full resolution image the radiologist is able to focus on the specific area that is described by the characteristics. This correlation of ROI characteristics with any of a variety of radiologist selected image clippings 510 can then be used in during future examinations to quickly focus in on individual areas that may need review. One example would be clipping a view of an abnormality that the radiologist recommended be reviewed after six or twelve months for any changes in size or appearance.

Additionally, the system provides for the clipping of various modalities of images. In addition to the mammogram images as shown in the ROI Gallery 500, additional images such as ultrasound or MRI captures can also be included in the gallery. One embodiment of this system can employ the storage of individual image clippings 510 in a compressed image format, such as the JPEG image format established by the Joint Photographic Experts Group, or another appropriate standard. The use of a compressed image format provides an acceptable resolution for a thumbnail image for an initial investigation, while requiring less storage space than a high-resolution image format, such as the DICOM format. The system also provides a link from the compressed image clippings 510 to the full-sized high-resolution image for the situations, such as making a diagnostic assessment, that require a radiologist to view the high-resolution image.

In one embodiment of the system, a database of thumbnail or clipped images can provide a source of investigational data that may assist a radiologist in categorizing an abnormality that he or she is unfamiliar with, or for use as a training tool. The association of the ROI categorizations with the clipped images also provides an efficient mechanism to search for individual image clippings 510 of a particular type of abnormality or to provide a convenient link to pathology reports or patient correspondence. Non-image based information such as patient correspondence or reports can be stored in the ROI Gallery 500 either in their native format or in an image format, such as JPEG, TIFF, GIF, or another appropriate standard, derived from a screen-capture of the report or document.

Figure 8A:
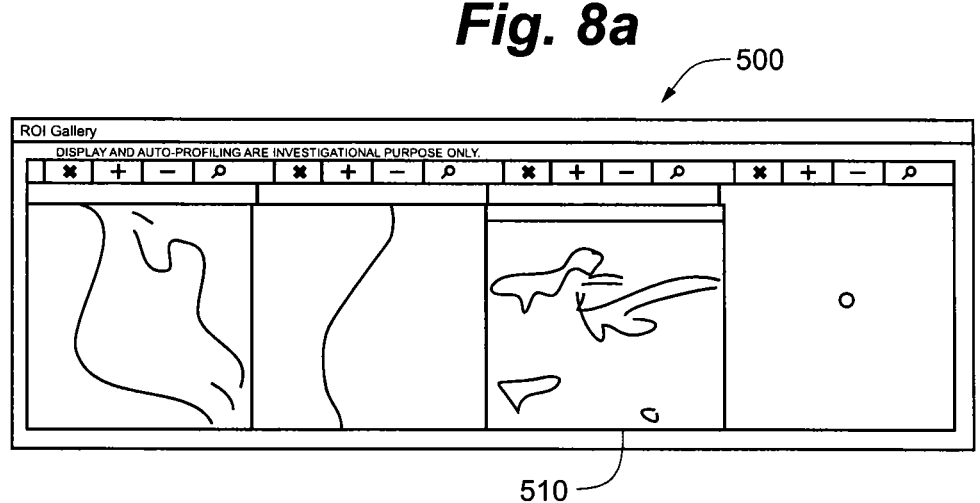
FIG. 8a is an another depiction of the ROI gallery window of FIG. 7.
Figure 8B:
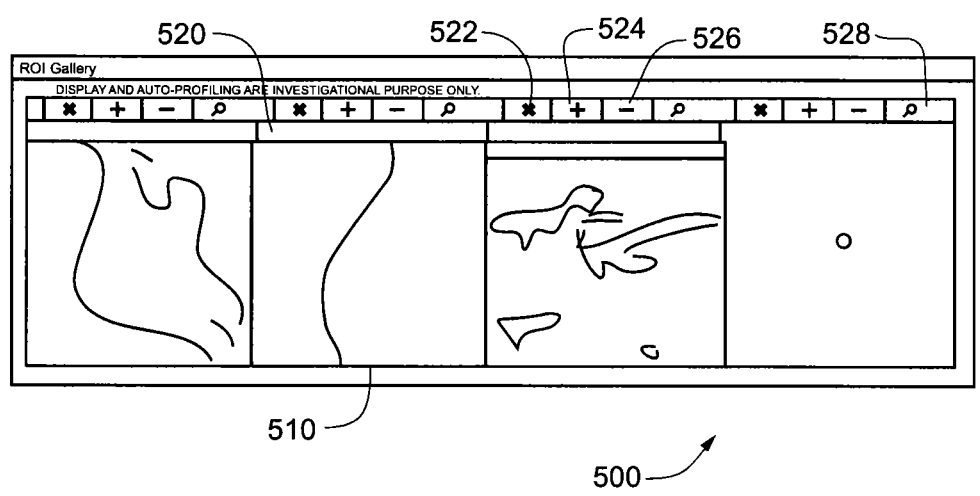
FIG. 8b is another example of a ROI gallery window for use with embodiments of this invention.

FIG. 8a is another depiction of ROI Gallery 500. Image clipping 510, as well as other images, can be attached or associated directly to an abnormality such as ROI is depicted by the craniocaudal mark 252. FIG. 8b depicts of ROI Gallery 500 with a single highlighted image clipping 510 as indicated by highlight-bar 520. Various exemplary tools are shown in ROI Gallery 500 that provide for the manipulation of individual image clippings. When an image is associated to an abnormality the title bar 520 changes color indicating a direct association. Tapping the "+" 524 provides a mechanism to attach image to abnormality 510. Tapping "−" 526 disassociates image clipping 510 if attached to a ROI. A double-click on image clipping 510 or tapping on magnification button 528 brings up an individual ROI viewer 550 to allow a large view along with access to other imaging tools.

Within the title bar the description of the view is display from the image it was obtained from for example RCC (RightCranioCaudal) image. In a contemplated embodiment, if the image was processed through a CAD tool the feature descriptors, such as CAD generated ROI outlines provided by that tool, are displayed. In another embodiment feature descriptors can be superimposed as an overlay on top of the image. Alternatively a hovering tool bar tool—for example when a user leaves the mouse cursor over an image a small message appears describing the area. Additionally, in order to reduce right/left errors when associating images to an ROI the imaging gallery does not allow right ROI to be associated to left breast abnormality and a left ROI is not allowed to be associated with a right breast image or abnormality.

As depicted, a user can delete 522 the image clipping 510 or open the image clipping 510 in an individual ROI viewer upon the selection of magnification button 528.

FIG. 9 depicts an example embodiment of a ROI viewer 550 depicting an individual image 552. The ROI viewer 550 provides additional image manipulation tools, including an "invert" selector 554 that replaces the black pixels for white and the white pixels for black. The ROI viewer 550 also provides a "3D" button 556 that can support the activation of a separate 3D-modeling software package that enables the radiologist to view and rotate a composite three-dimensional image of the associated ROI. The radiologist may return to the ROI Gallery 500 by selecting either the "Exit" button 558 or the "Close Window" icon 560.

The foregoing descriptions present numerous specific details that provide a thorough understanding of various embodiments of the invention. It will be apparent to one skilled in the art that various embodiments, having been disclosed herein, may be practiced without some or all of these specific details. In other instances, known components have not been described in detail in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention. It is manifestly intended that this invention be limited only by the following claims and equivalents thereof For purposes of interpreting the claims for the present invention, it is expressly intended that the provisions of Section 112, sixth paragraph of 35 U.S.C. are not to be invoked with respect to a given claim unless the specific terms "means for" or "step for" are recited in that claim.

Any incorporation by reference of documents above is limited such that no subject matter is incorporated that is contrary to the explicit disclosure herein. Any incorporation by reference of non-priority documents above is further limited such that no claims included in the documents are incorporated by reference herein and any definitions provided in the documents are not incorporated by reference herein unless expressly included herein.

The invention claimed is:

1. A computer-implemented method for managing patient mammography data comprising:
   obtaining a first breast tissue image according to an imaging modality, wherein the imaging modality is at least one of radiological, X-ray, computed tomography, ultrasound, magnetic resonance, or tomosynthesis;
   selecting a computer aided diagnostic (CAD) module based on the imaging modality;
   isolating, with the CAD module, a region of the first breast tissue image, the region containing an abnormality;
   categorizing the abnormality according to an established lexicon;
   populating lexicon descriptors for the categorized abnormality;
   storing an offset location of the selected region within the first image to define a second image, the offset location comprising coordinates relative to the first image;
   associating the second image with the categorized abnormality;
   correlating the second image with a location on an anatomical diagram, the anatomical diagram comprising a craniocaudal view and a mediolateral view of both left and right breasts of the patient; and
   generating a mark on the craniocaudral view and the mediolateral view, where visible on the craniocaudal view or mediolateral view, corresponding to the correlated location of the second image, wherein the mark can subsequently be selected to recall the second image to provide the second image for viewing.

2. The computer-implemented method of claim 1, further comprising associating a report with the categorized abnormality.

3. The computer-implemented method of claim 1, further comprising associating a copy of a patient correspondence letter with the categorized abnormality.

4. The computer-implemented method of claim 1, further comprising associating a biopsy result related to the abnormality with the categorized abnormality.

5. The computer-implemented method of claim 1, wherein the first breast tissue image is at least one image selected from one of the group consisting of: an X-ray image, a CT image, a MRI image, a pathological image and an ultrasound image.

6. The computer-implemented method of claim 1, further comprising retrieving the first breast tissue image based on a link between the first breast tissue image and the second image.

7. The computer-implemented method of claim 1, wherein the selected region of the first breast tissue image includes a region of interest.

8. The computer-implemented method of claim 7, further comprising:
   associating the second image with the categorization of the region of interest.

9. The computer-implemented method of claim 7, further comprising:
   retrieving the second image based on a request for a set of data including the categorization of the region of interest.

10. The computer-implemented method of claim 1, further comprising:
    obtaining at least one additional image including information related to a patient associated with the first breast tissue image;
    manually selecting a region of the at least one additional image;

storing a second offset location of the selected region within the at least one additional image to define a third image.

11. The computer-implemented method of claim 10, wherein the at least one additional image comprises text.

12. The computer-implemented method of claim 10, wherein the at least one additional image is selected from the group consisting of an X-ray image, a CT image, a MRI image, an ultrasound image, a pathology image, a pathology report, a reporting letter, and a portion of a medical file.

13. The computer-implemented method of claim 10, further comprising displaying thumbnail images of at least one of the first mammographic image, the second image, the at least one additional image and the third image.

14. The computer-implemented method of claim 1, wherein the offset location comprises coordinates including a first number of pixel spaces from a first edge of the first breast tissue image and a second number of pixel spaces from a second edge of the first breast tissue image.

15. The computer-implemented method of claim 1, wherein generating a mark on the craniocaudral view and the mediolateral view comprises manually marking the location on the anatomical diagram.

16. The computer-implemented method of claim 1, wherein generating a mark on the craniocaudral view and the mediolateral view comprises marking the location on the anatomical diagram based on an estimation by a computer aided diagnostic tool.

17. A configurable mammography diagnostic system, comprising:
   a plurality of electronic displays, at least one of the plurality of electronic displays configured to display a breast tissue image having at least one region of interest, the breast tissue image comprising an imaging modality of at least one of radiological, X-ray, computed tomography, ultrasound, magnetic resonance, or tomosynthesis; and
   a processor interfaced with data storage containing instructions executable by the processor that, when executed, cause the processor to:
      select a computer aided diagnostic (CAD) module based on the imaging modality;
      isolate, with the CAD module, the at least one region of interest of the breast tissue image;
      present a graphical user interface configured to be displayed on at least one of the plurality of electronic displays and comprising an anatomical diagram on which the at least one region of interest can be marked, the anatomical diagram comprising a craniocaudral view and a mediolateral view of both left and right breasts of the patient,
      present a clipping tool with which a portion of the breast tissue image including the at least one region of interest and displayed on at least one of the plurality of electronic displays can be manually selected as a second image, the second image displayable on at least one of the plurality of electronic displays as a subset of the breast tissue image,
      store an offset location of the second image within the breast tissue image as the second image, the offset location comprising coordinates relative to the breast tissue image,
      link the second image to the breast tissue image,
      categorize the region of interest according to an established lexicon,
      populate lexicon descriptors for the categorized region of interest, and
      associate the second image with a corresponding mark on the craniocaudral view and the mediolateral view, where visible on the craniocaudral view or mediolateral view, wherein the mark can subsequently be selected to recall the second image to provide the second image for viewing.

18. The configurable mammography diagnostic system of claim 17, wherein the system is connected to the image database by a network.

19. The configurable mammography diagnostic system of claim 17, wherein the breast tissue image is of a type selected from the group consisting of an X-ray image, a MRI image, an ultrasound image, a CT image, and a pathology image.

20. The configurable mammography diagnostic system of claim 17, wherein the graphical user interface is configured to present the second image based on a selection of the corresponding region of interest marked on the anatomical diagram.

21. The configurable mammography diagnostic system of claim 17, wherein the graphical user interface is configured to present the second image based on a request for a set of data including the categorization of the region of interest.

22. A computer-implemented method of correlating multiple image modalities comprising:
   obtaining a first mammographic image according to an imaging modality, wherein the imaging modality is at least one of radiological, X-ray, computed tomography, ultrasound, magnetic resonance, or tomosynthesis;
   selecting a computer aided diagnostic (CAD) module based on the imaging modality;
   isolating, with the CAD module, a region of interest of the first mammographic image., the region of interest containing an abnormality;
   categorizing the abnormality according to an established lexicon;
   populating lexicon descriptors for the categorized abnormality;
   obtaining a second mammographic image, wherein the second mammographic image is of a different modality than the first mammographic image;
   manually selecting a region of the first mammographic image;
   storing an offset location of the selected region within the first mammographic image to define a third image, the offset location comprising coordinates relative to the first mammographic image;
   manually selecting a region of the second mammographic image;
   storing a second offset location of the selected region within the second mammographic image to define a fourth image, the second offset location comprising coordinates relative to the second mammographic image;
   associating the third image with an anatomical diagram, the anatomical diagram comprising a craniocaudral view and a mediolateral view of both left and right breasts of the patient;
   associating the fourth image with the anatomical diagram;
   associating the third image with the categorization of the abnormality;
   associating the fourth image with the categorization of the abnormality;
   generating a mark on the craniocaudral view and the mediolateral view, where visible on the craniocaudral view or mediolateral view, corresponding to the association of the third image with the anatomical diagram;

generating a mark on the craniocaudral view and the mediolateral view, where visible on the craniocaudral view or mediolateral view, corresponding to the association of the fourth image with the anatomical diagram; and presenting the third image and the fourth image in a gallery based on a selection of the region of interest.

* * * * *